United States Patent
Cornelissen et al.

(10) Patent No.: US 7,582,703 B2
(45) Date of Patent: Sep. 1, 2009

(54) CROSS-LINKABLE COMPOUNDS COMPRISING A PERFLUOROPOLYETHER MOIETY

(75) Inventors: Ronald Hubert Carlos Cornelissen, Helmond (NL); Karel Pieter Daniël Van Zeeventer, Grashoek (NL); Peter Richard Markies, Grubbenvorst (NL); Guy Peter Maria Verbeek, Maaseik (BE); Joannes Adrianus Verbunt, Velden (NL); Sandra Mei-Iing De Jong, Venlo (NL); Peter Maria Cornelis Zeelen, Maashree (NL)

(73) Assignee: Oce-Technologies B.V., Venlo (NL)

( * ) Notice: Subject to any disclaimer, the term of this patent is extended or adjusted under 35 U.S.C. 154(b) by 778 days.

(21) Appl. No.: 10/626,695

(22) Filed: Jul. 25, 2003

(65) Prior Publication Data
US 2009/0069502 A1     Mar. 12, 2009

(30) Foreign Application Priority Data
Jul. 26, 2002     (EP) .................... 02078182

(51) Int. Cl.
*C08F 114/18* (2006.01)
(52) U.S. Cl. .................... 525/326.2; 521/145; 521/149; 525/104; 528/15
(58) Field of Classification Search ............. 525/326.2, 525/104; 528/15; 521/145, 149
See application file for complete search history.

(56) References Cited

U.S. PATENT DOCUMENTS

| 4,440,918 | A |   | 4/1984  | Rice et al. .................... 526/246 |
| 4,565,714 | A | * | 1/1986  | Koshar ....................... 427/515 |
| 5,026,606 | A |   | 6/1991  | Isbrandt et al. ............. 428/421 |
| 5,742,889 | A |   | 4/1998  | Tazelaar et al. ............. 399/308 |
| 5,837,774 | A | * | 11/1998 | Tarumi et al. ................ 525/104 |
| 6,160,030 | A | * | 12/2000 | Chaouk et al. ............... 521/145 |
| 6,673,887 | B2| * | 1/2004  | Yamaguchi et al. ........... 528/15 |

FOREIGN PATENT DOCUMENTS

| EP | 0 770 634 A2 |   | 10/1996 |
| EP | 1384742 A1   | * | 1/2004  |

* cited by examiner

*Primary Examiner*—Peter D. Mulcahy
*Assistant Examiner*—Henry Hu
(74) *Attorney, Agent, or Firm*—Birch, Stewart, Kolasch & Birch, LLP

(57) ABSTRACT

The invention pertains to a cross-linkable compound comprising a perfluoropolyether (PFPE) moiety derived from an hydroxy-terminated PFPE-oil, which is bonded through a spacer with an ethylenically unsaturated group, wherein the spacer extends over at least three carbon atoms. The invention further relates to a perfluoropolyether rubber obtainable by hydrosilating said cross-linkable compound and to an apparatus for transferring a toner image from an image-forming medium to a receiving medium.

6 Claims, No Drawings

CROSS-LINKABLE COMPOUNDS COMPRISING A PERFLUOROPOLYETHER MOIETY

CROSS-LINKABLE COMPOUNDS COMPRISING A PERFLUOROPOLYETHER MOIETY

This non-provisional application claims priority under 35 U.S.C. 119(a) on European Patent Application No. 02078182.9, filed in the European Patent Office on Jul. 26, 2002, the contents of which are hereby incorporated by reference.

The invention pertains to a cross-linkable compound comprising a perfluoropolyether (PFPE) moiety which is ultimately terminated by an oxygen atom and bonded through a spacer attached to the said oxygen atom with an ethylenically unsaturated group. The invention further pertains to a perfluoropolyether rubber obtainable by hydrosilating said cross-linkable compound and to an apparatus for transferring a toner image from an image-forming medium to a receiving medium comprising said perfluoropolyether rubber.

Cross-linkable compounds comprising PFPE are known in the art, for instance from U.S. Pat. No. 4,565,714 that describes a low surface energy material that is a hydrosilation reaction product of a compound containing fluorine and aliphatic unsaturation with a compound containing silicon-bonded hydrogen. Such compositions can be cured to a low surface energy material that in coating form is effective as a release surface for use with the most aggressive class of adhesives known in the art or for other applications requiring low adhesion. These compounds have a linking group that connects the unsaturation with the polymer and is, for example, selected from esters, amides, urethanes, and ethers such as —$CH_2$—O—, —$CH_2$—NH—(C=O)—, —$CH_2$—NH(C=O)—O—, and —($CH_2$)-[—($CH_2$)—]N(C=O)—, wherein the unsatuiation is vinyl (—CH=$CH_2$) or an alkyl or phenyl substituted derivative thereof. The present invention pertains to compounds that are derived from PFPE moieties that are hydroxy-terminated, commonly known as hydroxy-terminated PFPE-oils. These hydroxy-terminated PFPE oils can be easily coupled, through reaction with the hydroxy group, to an ethylenically unsaturated group as known in the art. This leads to the compound as worded in the above introduction. These compounds appear to be particularly useful for anti-stick purposes. For instance, methylol-terminated perfluoropolyethers can serve as a basis for making the compounds to which the present invention pertains. These PFPE compounds are disclosed as intermediates to other monomers and are prepared by reduction of esters, e.g., by reaction with lithium aluminum hydride or sodium borohydride. Reaction of these alcohols with ethylenically unsaturated halides, e.g., allyl bromide, in the presence of sodium hydride or potassium hydroxide provides ethylenically unsaturated PFPE's. It was, however, found that the known low surface energy materials deteriorate after a couple of months, especially when used at elevated temperatures, leading to loss of their non-sticking properties. This phenomenon is especially undesired when the rubber is applied in top layers of apparatuses for transferring a toner image from an image-forming medium to a receiving medium.

Apparatuses for transferring a toner image from an image-forming medium to a receiving medium are known, for instance from U.S. Pat. No. 5,742,889, which is incorporated by reference. The top layer in such apparatus is provided with a rubber that is obtained form reacting PFPE oil with a chain lengthener. However, the rubbers disclosed in this patent do not show the desired non-sticking properties after a number of months at elevated working temperatures.

It is therefore an objective of the present invention to provide a perfluoropolyether (PFPE) oil that can be used for making perfluoropolyether rubbers, that are particularly suitable for use in top layers of apparatuses for transferring a toner image from an image-forming medium to a receiving medium, and that preserve their non-sticking properties for much longer times at elevated temperatures.

It has now been surprisingly found that this objective, and other objectives for obtaining suitable rubbers, such as good visco-elastic properties including high elasticity and low compression set, is met with the above cross-linkable compounds when the spacer extends over at least three atoms between the oxygen atom and the ethylenically unsaturated group. Thus, the "distance" between the oxygen atom which terminates the compound comprising the PFPE-moiety and the ethylenically unsaturated group involves at least three atoms in a row. As a result, good monomers for providing suitable rubbers can be obtained.

In one embodiment, the spacer extends over at least four atoms. It has been found that this embodiment can provide monomers that lead to even better rubbers.

In another embodiment, the atoms of the spacer are carbon atoms. This surprisingly leads to rubber materials having better anti-stick properties.

Yet another embodiment pertains to compounds having the formula:

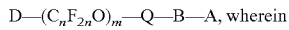

A stands for an ethylenically unsaturated group of the formula $HR_1C=CR_2R_3$, wherein $R_1$ is selected from H, alkyl, phenyl, alkyl-substituted phenyl and aralkyl; $R_2$ is selected from H, alkyl, phenyl, alkyl-substituted phenyl and aralkyl, and $R_3$ is a bond or $Si(R_4)_2$, $R_4$ being independently H or alkyl;

B stands for a hydrocarbyl or fluorocarbylspacer extending over at least three carbon atoms;

$(C_nF_{2n}O)_m$ is the PFPE moiety wherein n is independently an integer of 1 to 4 and m is an integer of 2 to 500;

Q is a group selected from $CF_2$—$CH_2$—O, $CH_2$—$CH_2$—O; and

D stands for HO—$CH_2CF_2$—O— or A—B—Q—O—, wherein n, A, B, and Q have the previously given meanings.

In the above definition, "alkyl" is preferably a branched or unbranched alkyl group with 1 to 4 carbon atoms, such as methyl, ethyl, propyl, isopropyl, n-butyl, isobutyl, sec-butyl and the like. The alkyl group in the substituted phenyl preferably has the same meaning. The term "aralkyl" means an aryl substituted alkyl group, wherein the branched or unbranched alkyl group preferably has 1 to 6 carbon atoms and the aryl group preferably is phenyl.

In the formula $(C_nF_{2n}O)_m$ for the PFPE moiety, "n" is independently selected. Thus, this formula includes both homopolymers (wherein the values "n" are the same for each recurring monomeric unit) and co-polymers, wherein the PFPE moiety is built up of different recurring monomers with different values of "n", for instance PFPE moieties that are built from both ($CF_2O$) and ($CF_2CF_2O$) recurring units. Preferably, the PFPE moiety has a molecular weight of about 1,000 to 20,000. Thus, preferably, dependent on the molecular weight of the monomeric units, m is preferably between 4 and 300. Such PFPE moieties are known in the art, for instance from US Pat. Appln. No. 2001/0008916 A1, which is incorporated by reference.

The above compounds can be hydrosilated by bringing about a condensation of a silicon-hydrogen-containing compound with the ethylenically unsaturated PFPE compound, preferably in the presence of a hydrosilating catalyst.

"Hydrosilation" means a reaction involving the addition of a silicon-hydrogen group across a pair of aliphatic unsaturated carbon atoms, i.e., carbon atoms joined by double bonds. The reaction can be illustrated by the following general equation:

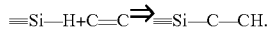

"Perfluoropolyether" ("PFPE") in the sense of the invention means a polyether, i.e. a compound comprising a chain of at least two alkoxy groups. The alkylene groups, which can be branched or are straight chains are completely, or at least to a substantial extent, fluorinated. The PFPE might occasionally comprise alkylene groups which are not completely fluorinated. In particular embodiments, the alkylene groups contain 1 to 6, preferably 1 to 4, carbon atoms but the invention is not restricted to such, groups.

The hydrosilation catalysts employed in the compositions of the present invention include all of the well-known metal-containing catalysts, which are effective for catalyzing a hydrosilation reaction between silicon-bonded hydrogen groups and ethylenically unsaturated groups. These materials include, for example, the finely divided platinum catalysts, such as those described in U.S. Pat. No. 2,970,150, the chloroplatinic acid catalysts described in U.S. Pat. No. 2,823,218, the platinum hydrocarbon complexes taught in U.S. Pat. Nos. 3,159,601 and 3,159,662 as well as the platinum alcoholate catalysts described in U.S. Pat. No. 3,220,972, the platinum complexes having an ultraviolet displaceable group such as are disclosed in U.S. Pat. No. 4,530,879 and the (cyclopentadienyl)(trialiphatic)platinum complexes such as are disclosed in U.S. Pat. No. 4,510,094. In addition, the platinum chloride-olefin complexes described in U.S. Pat. No. 3,416,946 are useful herein. A suitable catalyst is a platinum catalyst solution of ABCR, SIP 6832 in a concentration of 3 to 50 ppm on a weight basis. All of the teachings of hydrosilation catalysts in the aforesaid U.S. patents are incorporated herein by reference.

The composition of the invention can also contain other ingredients such as hydrosilation inhibitors, dyes, pigments and reinforcing fillers, e.g., carbon black, fumed silica, titanium dioxide, etc. Furthermore, the release character of the cured composition can be modified, i.e., the value of the force required to separate an adhesive from the surface of the cured composition can be modified by any method known in the art, e.g., by the method described previously, by the addition to the composition of 0.1 to 10 parts of a release modifier per 100 parts of the composition, or by use of different primers. Preferably, the release modification provides a differential release of at least 10 percent. Such modifiers are known and include, for example, tetraalkoxyalkyl silicates such as $Si(OC_2H_4OC_2H_5)_4$, such as are described in U.S. Pat. No. 3,518,325; graft polymers having a polyorganosiloxane segment and an organic polymer segment as are described in U.S. Pat. No. 4,366,286; vinyl terminated diorganopolysiloxanes in which 3 to 39 mole percent of the diorgano units are non-terminal diphenylsiloxane units; and the three-dimensional toluene soluble silicate resins, known in the silicate art as MQ resins which are described in U.S. Pat. Nos. 2,676,182 and 2,857,356.

Suitable cross-linkable compounds according to the invention can be made, for instance, as follows:

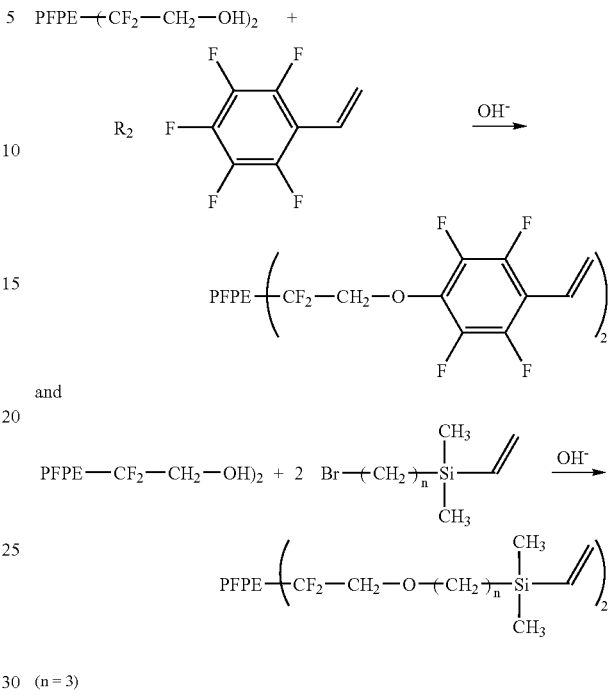

$(n = 3)$ whereas from the prior art it is known to make a cross-linkable compound for instance as follows:

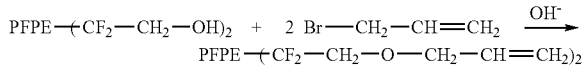

In these formulae, PFPE represents any PFPE as indicated above. In the first example of an embodiment according to the invention, the spacer extends over 4 carbon atoms (between the ultimate oxygen atom and the ethylenically unsaturated group). In the second example the spacer extends over 3 carbon atoms+1 silicon atom. It has been found that a spacer extending over at least three atoms, in particular carbon atoms, between the oxygen atom and the silicon atom, lead to excellent rubbers. The prior art shows a spacer extending over 1 carbon atom.

The above silylalkylbromide intermediate compound is novel and can be made according to the following scheme (for example when n=4):

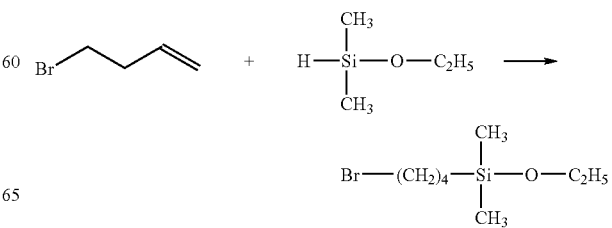

-continued

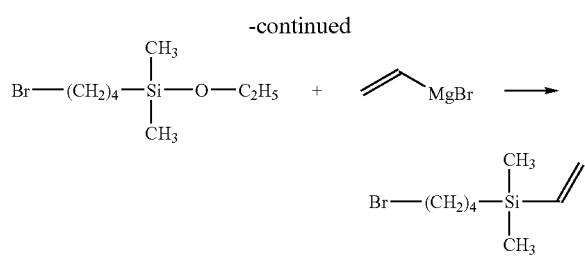

End groups that can very suitably be coupled to a hydroxy group of the linking group are, for instance,

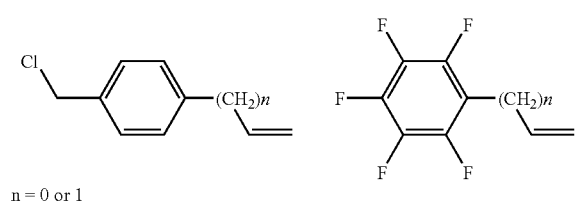

n = 0 or 1

The unsaturated bond of these end groups can be hydrosilated (vulcanization) with a multi-SiH cross-linker to form a silylated compound with a spacer between the unsaturated group (vinyl) and the oxygen atom of the linking group of at least 3 carbon atoms to obtain a stable bond.

Suitable SiH cross-linkers are methyl tris(dimethylsiloxy) silane ['T(Mh)3'], cyclo(tetramethyltetrasiloxane) and homologs thereof ['(Dh)x'], short linear siloxane derivatives ['M(Dh)nM'], tetrakis(dimethylsiloxy)silane ['Q(Mh)4'] and higher oligomers thereof ['Qn(Mh)m'], To the vinyl terminated PFPE oil is added subsequently an inhibitor for obtaining sufficient pot life for good processing. A suitable inhibitor is 1-ethynylcyclohexanol ['ECH'] in a weight ratio of 500-5000 ppm relative to the oil. The inhibitor is injected pure in melted form using a microliter syringe.

A SiH cross-linker is added in an amount of 1.5-3 equivalents of SiH groups with regard to the vinyl groups in the PFPE oil. If necessary for a better mixability, a quantity of a solvent may be added, for instance, 1,3-bis(trifluormethyl) benzene ['fluoroxylene']. After completion of mixing, a hydrosilation catalyst is added, in a concentration of about 5-50 ppm.

After mixing, for instance with a mechanical stirrer, and degassing by evacuation, the mixture can be cross-linked (cured) in the air (coatings) or, when no solvent is used, in a mold at 120-140° C. Curing usually takes 1-10 minutes. Further curing may take place in the air overnight at 120° C. The hardness then further increases due to evaporation of the solvent, oxidation and coupling of excess SiH groups.

It is also possible to apply a pre-curing of part of the PFPE oil with excess of SiH cross-linker (about 2-5 moles of SiH cross-linker per vinyl group). This is particularly useful when the mixing of PFPE oil and SiH cross-linker is insufficient. Pre-curing is for instance performed at 120° C. for 0.5 h under nitrogen atmosphere in 1,3-bis(trifluorobenzene) as solvent. The 'alloy' of PFPE oil with SiH reactive silicones is obtained after evaporation of the solvent and can be stored under nitrogen.

When this reagent is strongly opaque and a silicone fraction separates, an effective separation can be achieved by extraction with low-molecular PFPE solvent ['HT 70'] and cyclohexane. A mixture of crude pre-cured product and 1 part of PFPE solvent can be separated from a silicon fraction by extraction with 1 part of cyclohexane.

The invention also relates to an apparatus for transferring a toner image from an image-forming medium to a receiving medium comprising:

an endless movable intermediate medium including a support provided with a top layer secured to the support via a rear surface, the intermediate medium being in contact with the image-forming medium in a first transfer zone;

heating means for heating the toner image on the top layer of the intermediate medium;

a biasing means for contacting the intermediate medium in a second transfer zone; and transport means for transporting the receiving medium through the second transfer zone, wherein the top layer comprises a perfluoropolyether rubber which is obtainable by hydrosilating a cross-linkable compound comprising a perfluoropolyether (PFPE) moiety which is ultimately terminated by an oxygen atom and bonded through a spacer attached to the said oxygen atom with an ethylenically unsaturated group, wherein the spacer extends over at least three atoms between the oxygen atom and the ethylenically unsaturated group.

The invention is further illustrated with the following non-limitative examples.

EXAMPLE 1

4-Bromobutyl-dimethyl-ethoxysilane 800 g of 4-bromo-1-butene were reacted with 15% excess of dimethylethoxysilane (939 ml). In a 2 l reactor 0.5 g of $Ru_3(CO)_{12}$ and 800 ml of 4-bromo-1-butene were brought under nitrogen and 939 ml of dimethylethoxysilane were added under nitrogen and the mixture was brought at 65° C. After 0.5 h the bath temperature was raised to 80° C. and the mixture was allowed to react overnight. After distillation 1329 g (93.7%) of 4-bromobutyl-dimethyl-ethoxysilane were isolated.

4-Bromobutyl-dimethyl-vinylsilane

A 3 l reactor was charged under nitrogen with 1 l of vinyl magnesium bromide in THF (tetrahydrofuran) and 184 g of 4-bromobutyl-dimethyl-ethoxysilane were added slowly at room temperature. The mixture was then refluxed at 70° C. for 16 h. After cooling on ice, the mixture was quenched with 407 g of a 20% HBr (w/w) solution, after which it was stirred for another 1.5 h. The THF layers were separated from the aqueous layers and neutralized with aq. sodium hydrogen carbonate solution. The THF was evaporated and the residue was distilled in the presence of 1 g Pt/C to obtain 135.8 g (79.8%) of pure 4-bromobutyl-dimethyl-vinylsilane

EXAMPLE 2

Coupling of 4-bromobutyl-dimethyl-vinylsilane to PFPE-oil

A 1 l reactor was charged with 200 g (91 mmole) of OH-terminated PFPE-oil (Fluorlinl; D, from Ausimont s.p.a.), 220 ml of 1,3-bis(trifluoromethyl)benzene and 48.2 g (218 mmole) of 4-bromobutyl-dimethyl-vinylsilane. The mixture was heated at 70° C. under stirring until a clear colorless solution was obtained, after which a mixture of 43.3 g of a 47% KOH solution, 160 ml of water and 8 g of tetrabutylammonium hydroxide was added dropwise. After reacting for 4 h at 10° C., the aqueous layer was separated after which a fresh mixture of 43.3 g of a 47% KOH solution, 160 ml of water and 8 g of tetrabutylammonium hydroxide were added and stirred for another 16 h at 100° C. The mixture was cooled down and the water layer was separated. The reaction mixture was washed with water, glacial acetic acid and methanol. The oily residue was concentrated and stirred with 15 g of polyvinylpyridine and 100 ml of HT™70 (a non-reactive PFPE-oil with a boiling point of 70° C., from Ausimont s.p.a.) for 3 days. After filtering and evaporation to dryness, a colorless oil was obtained, more than 99% of which was coupled to the end group.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A cross-linkable compound comprising a perfluoropolyether (PFPE)-containing moiety which is ultimately terminated by an oxygen atom and bonded through a spacer attached to the said oxygen atom with an ethylenically unsaturated group, wherein the spacer extends linearly over at least three atoms in a row between the oxygen atom and the ethylenically unsaturated group, said cross-linkable compound having the formula

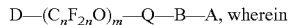
D—($C_nF_{2n}O$)$_m$—Q—B—A, wherein

A stands for an ethylenically unsaturated group selected from the group consisting of $HR_1C$=$CR_2$— and $HR_1C$=$CR_2Si(R_4)_2$—, wherein $R_1$ is selected from H, alkyl, phenyl, alkyl-substituted phenyl and aralkyl; $R_2$ is selected from H, alkyl, phenyl, alkyl-substituted phenyl and aralkyl and $R_4$ being independently H or alkyl;

B stands for a hydrocarbyl or fluorocarbyl spacer extending over at least three carbon atoms;

($C_nF_{2n}O$)$_m$ is the PFPE moiety wherein n1 is independently an integer of 1 to 4 and m is an integer of 2 to 500;

Q stands for a bivalent group selected from —$CF_2$—$CH_2$—O— and —$CH_2$—$CH_2$—O—; and D stands for HO—$CH_2CF_2$—O— or A—B—Q—O—, wherein n, A, B, and Q have the previously given meanings.

2. A compound according to claim 1, wherein the spacer extends over at least four atoms.

3. A compound according to claim 1 or claim 2, wherein the atoms of the spacer are carbon atoms.

4. The cross-linkable compound of claim 1 or claim 2 wherein the hydrocarbyl spacer extends over at least four carbon atoms.

5. The cross-linkable compound of claim 1 or claim 2 wherein A stands for $H_2C$=CH—.

6. The cross-linkable compound of claim 1 or claim 2 wherein D is A—B—Q—O—, Q stands for —$CF_2$—$CH_2$—O—, and B—A has the formula —$C_6F_4$—CH=$CH_2$ or —($CH_2$)$_o$—Si($CH_3$)$_2$—CH=$CH_2$, wherein o is 3 or 4.

* * * * *